(12) United States Patent
Devenyi et al.

(10) Patent No.: US 8,990,260 B2
(45) Date of Patent: Mar. 24, 2015

(54) REMOTE HEALTH MONITORING SYSTEM

(71) Applicant: General Electric Company, Schenectady, NY (US)

(72) Inventors: Csaba Devenyi, Budapest (HU); Roland Lohner, Budapest (HU)

(73) Assignee: General Electric Company, Schenectady, NY (US)

( * ) Notice: Subject to any disclaimer, the term of this patent is extended or adjusted under 35 U.S.C. 154(b) by 141 days.

(21) Appl. No.: 13/631,312

(22) Filed: Sep. 28, 2012

(65) Prior Publication Data

US 2013/0086122 A1 Apr. 4, 2013

(30) Foreign Application Priority Data

Sep. 30, 2011 (EP) .................................... 11462017

(51) Int. Cl.
 G06F 17/30 (2006.01)
 G06F 19/00 (2011.01)
(52) U.S. Cl.
 CPC .......... *G06F 19/345* (2013.01); *G06F 19/3418* (2013.01)
 USPC ........................................................ 707/797
(58) Field of Classification Search
 CPC .................... G06F 17/30625; G06F 17/30961
 USPC .......................................... 707/736, 778, 797
 See application file for complete search history.

(56) References Cited

U.S. PATENT DOCUMENTS

| | | | |
|---|---|---|---|
| 4,803,625 A | 2/1989 | Fu | |
| 4,838,275 A * | 6/1989 | Lee | 600/483 |
| 6,527,712 B1 * | 3/2003 | Brown et al. | 600/300 |
| 6,978,169 B1 * | 12/2005 | Guerra | 600/523 |
| 7,024,369 B1 * | 4/2006 | Brown et al. | 705/2 |
| 7,273,454 B2 | 9/2007 | Gordon et al. | |
| 7,310,668 B2 | 12/2007 | Brown | |
| 7,320,030 B2 | 1/2008 | Brown | |
| 7,399,276 B1 | 7/2008 | Brown | |
| 7,547,278 B2 | 6/2009 | Iwano et al. | |

(Continued)

OTHER PUBLICATIONS

J Boger, "A Planning System Based on Markoc Decision Processes to Guide People with Dementia Through Activities of Daily Living", IEEE Transactions on Information Technology in Biomedicine, vol. 10, No. 2, Apr. 1, 2006, pp. 323-333.

(Continued)

*Primary Examiner* — Cam-Linh Nguyen
(74) *Attorney, Agent, or Firm* — GE Global Patent Operation; Marc A. Vivenzio

(57) ABSTRACT

Health monitoring system comprising a patient side subsystem, a health care provider side subsystem, and a server station. The patient side subsystem is able to periodically receive and apply a monitoring profile comprising profile elements being connected to each other in a predetermined manner, the monitoring profile elements comprising patient related data, monitoring related data, evaluating process elements, wherein the monitoring profile elements are connected to each other to provide a multi-level tree structure consisting of at least two monitoring profile levels comprising a higher or top level and a lower or bottom level, wherein the monitoring profile elements are divided according to the tree structure of the multi level monitoring profile and a part of the monitoring profile elements is assigned to the top monitoring profile level and a part of the monitoring profile elements is assigned to the bottom monitoring profile level.

17 Claims, 4 Drawing Sheets

(56) References Cited

U.S. PATENT DOCUMENTS

| | | | |
|---|---|---|---|
| 7,624,028 B1 | 11/2009 | Brown | |
| 7,684,999 B2 | 3/2010 | Brown | |
| 8,388,530 B2* | 3/2013 | Shusterman | 600/300 |
| 2002/0077711 A1* | 6/2002 | Nixon et al. | 700/51 |
| 2003/0078810 A1* | 4/2003 | Cole et al. | 705/3 |
| 2003/0078811 A1* | 4/2003 | Cole et al. | 705/3 |
| 2003/0153818 A1* | 8/2003 | Bocionek et al. | 600/300 |
| 2003/0204789 A1* | 10/2003 | Peebles et al. | 714/47 |
| 2004/0078232 A1* | 4/2004 | Troiani | 705/2 |
| 2004/0097796 A1* | 5/2004 | Berman et al. | 600/310 |
| 2005/0043965 A1* | 2/2005 | Heller et al. | 705/2 |
| 2005/0222873 A1 | 10/2005 | Nephin et al. | |
| 2007/0050777 A1* | 3/2007 | Hutchinson et al. | 718/104 |
| 2007/0197881 A1 | 8/2007 | Caruso et al. | |
| 2008/0138832 A1* | 6/2008 | Ivey et al. | 435/7.1 |
| 2008/0140449 A1* | 6/2008 | Hayes | 705/2 |
| 2009/0015403 A1* | 1/2009 | Kuris et al. | 340/540 |
| 2009/0077055 A1* | 3/2009 | Dillon et al. | 707/5 |
| 2009/0089074 A1* | 4/2009 | Schoenberg | 705/1 |
| 2010/0064039 A9* | 3/2010 | Ginter et al. | 709/224 |
| 2010/0131874 A1* | 5/2010 | Linthicum et al. | 715/764 |
| 2011/0004110 A1* | 1/2011 | Shusterman | 600/509 |
| 2011/0010087 A1* | 1/2011 | Wons et al. | 701/201 |
| 2011/0125528 A1* | 5/2011 | Padate et al. | 705/3 |
| 2011/0225008 A1* | 9/2011 | Elkouh et al. | 705/3 |
| 2012/0143068 A1* | 6/2012 | Cheng et al. | 600/485 |
| 2012/0232931 A1* | 9/2012 | Buisman et al. | 705/3 |

OTHER PUBLICATIONS

Corchado et al.,"Intelligent Environment for Monitoring Alzheimer patients, agent technology for health care", Decision Support Systems, Elsevier Science Publishers, vol. 44, No. 2, Nov. 24, 2007, pp. 382-396, Amsterdam, NL.

Su et al., "JADE implemented mobile multi-agent based, distributed information platform for pervasive health care monitoring", Applied Soft Computing, vol. 11. No. 1, Jan. 1, 2011, pp. 315-325, Amsterdam, NL.

European Search Report from corresponding European Application No. 11462017.2, Dated Feb. 16, 2012.

* cited by examiner

REMOTE HEALTH MONITORING SYSTEM

CROSS-REFERENCE TO RELATED APPLICATIONS

This application claims foreign priority benefits under 35 U.S.C. §119 to co-pending European Patent Application Serial No. 11462017.2, filed Sep. 30, 2011, which is hereby incorporated by reference in its entirety as part of the present disclosure.

BACKGROUND OF THE INVENTION

Embodiments of the present invention generally relate to a remote health monitoring system, and, more specifically, to a system for automatic remote health monitoring, behavior monitoring, and therapy tracking.

There are many remote health monitoring systems on the market for monitoring the health condition, the behavior, or medication of patients that can be used in health care institutional or home environment.

In U.S. Pat. No. 7,624,028, a remote health monitoring and maintenance system and method that enable a health care provider to monitor and manage health conditions of a patient are described. The system includes a health care provider apparatus operated by a health care provider and a remotely programmable patient apparatus that is operated by a patient. The health care provider develops a script program using the health care provider apparatus and then sends the script program to a remotely programmable patient apparatus through a communication network such as the World Wide Web. The script program is a computer-executable patient protocol that provides information to the patient about the patient's health condition and that interactively monitors the patient health condition by asking the patient questions and by receiving answers to those questions. The answers to these health related questions are then forwarded as patient data from the remotely programmable patient apparatus to the health care provider apparatus through the communication network. The patient data may also include information supplied by a physiological monitoring device such as a blood glucose monitor that is connected to the remotely programmable patient apparatus. When the patient data arrives at the health care provider apparatus, the patient data is processed for further management of the patient's health condition by the health care provider, such as forwarding another script program to the remotely programmable patient apparatus.

U.S. Pat. No. 7,624,028 also describes a system, where healthcare providers are enabled to monitor health conditions of the patient. These conditions are collected by physiological monitoring devices connected to the patient side device, or by the patient side device itself, in form of surveys. Healthcare providers are also enabled to change the details, parameters, and the flow of inspection or therapy. The changes in monitoring and therapy details are automatically delegated to the patient device through the communication network. This prior art system allows some flexibility with respect to collecting patient related information but the initial setup and customization of compound patient monitoring and therapy tracking profiles and also every change regarding these profiles require an extensive programming/configuration step carried out by a health care provider or administrator. This programming/configuration requires special skills and may be rather time consuming, as well.

In U.S. Patent application no. 2005/0222873 A1, systems, methods and user interfaces for configuration of medical patient monitoring and configuration systems are disclosed. At a central database in which patient information, health care provider information and health care group information may be stored, patient information is associated with health care provider information, which is associated with health care group information. When stored information is accessed, patient information is displayed with its associated health care provider information, and health care provider information is displayed with its associated health care group information. Systems, methods, and user interfaces for customizing per-patient and standardized user prompts are also disclosed.

U.S. Patent application no. 2005/0222873 A1 discloses a system with elaborate user interface functionality, in which much valuable information is displayed when patient records are accessed. However the high amount of displayed low-level information regarding questionnaires, reminders, medications, health conditions, vital sign measurements, monitoring events can be confusing and can make difficulties in quick and accurate overview of the running therapy process and the current state of the patient.

As shown in the next paragraphs below, composition, configuration, and parameterization of more compound home monitoring and therapy profiles can be quite complicated in the prior art systems. The low-level composition of monitoring procedures and low-level setup of high amount of possible monitoring and therapy parameters presented above is an expert-demanding, time-consuming task.

The term patient will be used for an individual to be monitored, who is at a distant location from the medical assistance. Patients may live in his/her own house or flat or may be resident of an assisted living facility.

The term monitoring profile will be used as a set of monitoring and therapy processes running at the patient site, which is composed of predefined monitoring elements (templates) and which can be fully configured, customized and parameterized. A monitoring profile may be very complicated, as it may contain numerous elements of types of measurement specifications, monitoring procedures, signal processors, medical rules, surveys, and patient tasks.

A measurement specification describes a physiological measurement in all details. It includes the scheduling of the measurement, the used measurement device, the measurement instructions to display on the patient side device (also referred to as 'homehub'), and possibly surveys, which must be taken during, before, or after measurement.

A monitoring procedure describes the measurement procedure of a behavioral attribute in all details. It includes the applicable measurement devices, scheduling, and an algorithm, which calculates the behavioral attribute based on sensor data.

Signal processors are computing program modules, which are capable of processing physiological or behavioral data and generating higher order, derived data.

Medical rules are expert rules of human medical professionals, which are applied in an expert system, as a knowledge base of human expertise for problem solving, or clarify uncertainties.

Surveys are written set of questions, which can be displayed to the patient on the homehub in order to collect qualitative or quantitative information.

Patient tasks are tasks, which are displayed by the homehub and must be carried out by the patient with the purpose of testing a patient skill (e.g. cognitive test) or providing therapy (e.g. exercising).

When a new patient enters the health-monitoring provider, a new applicable monitoring profile must be set up. When the state of a patient changes, or a therapy must be changed, the applied monitoring profile must be reviewed and corrected. The task of monitoring profile management includes the composition, tracking of the monitoring elements and also their parameterization, like scheduling details (e.g. period of scheduling, day, hour, minute of run, number of repeats, day offs), limit values (e.g. limits of physiological values, behavioral attributes), delay, timeout values (in monitoring procedures many timeout values are used, for instance: maximal allowed minutes spent in bathroom before generating an alert), signal processor parameters (e.g. acceleration offset used in fall detection signal processor, or detailed settings of an ECG signal processor, like time delay of beginning of average computing after the base point), questions, and flow of survey (in case of surveys the flow (what to ask next after getting a certain answer) and questions itself can be defined), contact information (signal processors, surveys, medical rules are capable of generating monitoring events, monitoring alerts, which must be transferred to healthcare professionals or caregivers, where the contact information describes the recipient details of those alerts.)

The setting up of a monitoring profile means composing it from numerous monitoring elements of the types listed above and parameterizing these elements with the possible parameters listed above, as well. In case of multiple monitoring elements the setup may be very complicated.

On the other hand review of a running monitoring profile may be complicated, too. If the expert only sees the low-level monitoring elements, it is hard to put together all of them in mind in order to have a high-level overview.

Finally viewing, analyzing, and inspecting of low-level measurement data can be very complicated, also. For instance, the human overview of the low-level outputs of motion sensors, containing timestamps (e.g. time of motion event) and zone identifiers (e.g. place of motion) is hardly possible, regarding the high amount of motion data generated every day.

BRIEF SUMMARY OF THE INVENTION

According to an embodiment of the present invention, there is provided a health monitoring system comprising a patient side subsystem, a health care provider side subsystem, and a server station with a database and a communication system for providing communication links between the system elements, with the help of which the patient side subsystem is able to periodically receive and apply a monitoring profile consisting of profile elements being connected to each other in a predetermined manner, the monitoring profile elements comprising patient related data, monitoring related data, and evaluating process elements, wherein the monitoring profile elements are connected to each other to provide a multi level tree structure comprising at least two monitoring profile levels comprising a higher or top level defining a top-level monitoring profile, and a lower or bottom level containing the low-level monitoring profile elements, wherein the monitoring profile elements are divided according to the tree structure of the multi level monitoring profile and a part of the monitoring profile elements is assigned to the top monitoring profile level and a part of the monitoring profile elements is assigned to the bottom monitoring profile level.

According to an embodiment of the present invention, there is provided a method for operating a health monitoring system, wherein the monitoring system comprises a patient side subsystem, a health care provider side subsystem, a server station with a database and a communication system for providing communication links between the system elements. The method comprises providing a monitoring profile consisting of profile elements being connected to each other in a predetermined manner, the monitoring profile elements comprising patient related data, monitoring related data, and evaluation process elements, wherein the monitoring profile elements are connected to each other to provide a multi level tree structure consisting of at least two monitoring profile levels comprising a higher or top level defining a top-level monitoring profile adapted to a specific health status, and a lower or bottom level containing the low-level monitoring profile elements, wherein the monitoring profile elements are divided according to the tree structure of the multi level monitoring profile and a part of the monitoring profile elements is assigned to the top monitoring profile level and a part of the monitoring profile elements is assigned to the bottom monitoring profile level.

BRIEF DESCRIPTION OF THE DRAWINGS

These and other features, aspects and advantage of the embodiments of the present invention can be better understood when the following detailed description are read with reference to the accompanying drawings, in which.

DETAILED DESCRIPTION OF THE INVENTION

Due to the disadvantages of the prior art systems and methods, there is a continuous need for providing a system and a method, which effectively supports healthcare professionals in composition and customization of the whole monitoring profile, high-level overview, and change of a monitoring profile, high-level data presentation, and, through usage of predefined hierarchical, multi-level structures, so called multi-level monitoring profile (MMP) definitions.

Figure 1:
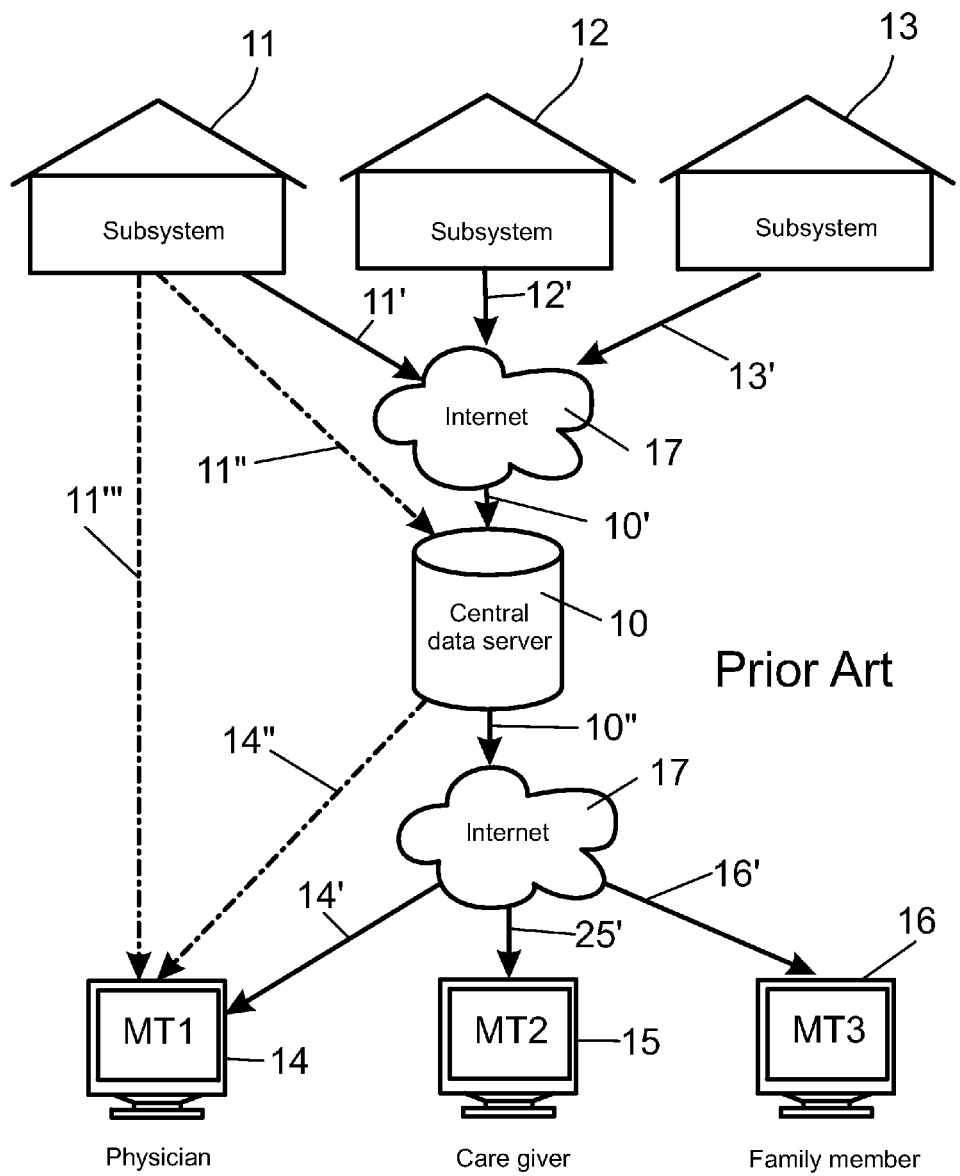
FIG. 1 is a schematic block diagram of the health monitoring system.

Referring first to FIG. 1, a schematic block diagram of a remote health monitoring system is shown. The system comprises a plurality of patient side subsystems 11, 12, 13 at the location of the individuals (or patients) to be monitored distant from medical assistance, such as in a home environment. In the simplest case, a subsystem, such as subsystem 11 may be connected to a health care provider side subsystem, comprising monitoring terminals 14, 15 or 16. In an embodiment, the subsystem 11 is connected to monitoring terminal 14 via a communication channel 11'''. The communication channel 11''' may be either a radio or a cable communication channel. In an embodiment, a monitoring person may have only access to one individual to be monitored at a time. Each change of the monitored person would require a reconnection to another communication channel. This problem can be solved by using a central communication and data server station 10 with a database, which is capable of communicating with the subsystems 11, 12, 13 via data communication channels, through a cable or an air interface. The monitoring terminals 14, 15, 16 are also capable of communicating with the central server station 10 in order to provide information for visual display to the monitoring persons, such as health care professionals and/or care giving personnel and/or authorized family members. Each group of the monitoring persons has a predetermined access right category to access monitoring information provided by the subsystems 11, 12, 13 and the central server unit 10. The health care professionals may for example be authorized to functionalities such as browsing patient data and setting up the monitoring parameters for the individual patient. The caregiver personnel may be authorized to browsing patient data and preparing different reports based on it. The family members may be authorized to have access to their respective relative in order to have information about his or her health condition. The monitoring terminals 14, 15, 16 may be connected to the central server 10 through either a radio communication channel or a cable communication channel, or a combination of a radio communication channel and a cable communication channel 14', 15', 16', such as the internet 17. The use of the internet 17 as a communication channel makes it possible to set up the elements of the remote health monitoring system at any location of the world without any limitation. Therefore in a most flexible configuration, the elements of the system, e.g. the subsystems 11, 12, 13 are connected through communication links 11', 12', 13', the central server unit 10 through communication links 10' and 10", and the monitoring terminals 14, 15, 16 through communication links 14', 15', 16' to the internet 17. In a general configuration of FIG. 1 the central server station 10 receives and stores all the data from the connected home hubs (subsystem control units) and provides access to information about the health condition of all individuals included in the system to the authorized monitoring persons. This system makes it also possible for the patient side subsystem to periodically receive and apply a monitoring profile consisting of profile elements being connected to each other in a predetermined manner. The monitoring profile elements comprise patient related data, such as configuration parameters, monitoring related data, such as configuration parameters, and evaluating process elements, such as software components responsible for the functionality of the monitoring profile elements.

In this configuration of the health monitoring system for determining and applying different monitoring profiles for the different patients, the patient side subsystem 11 to 13 may also comprise a subsystem control unit 20 and measuring units for performing continuous measurement of behavioral data of the individuals to be monitored or distinct measurements of vital signs.

Figure 2:
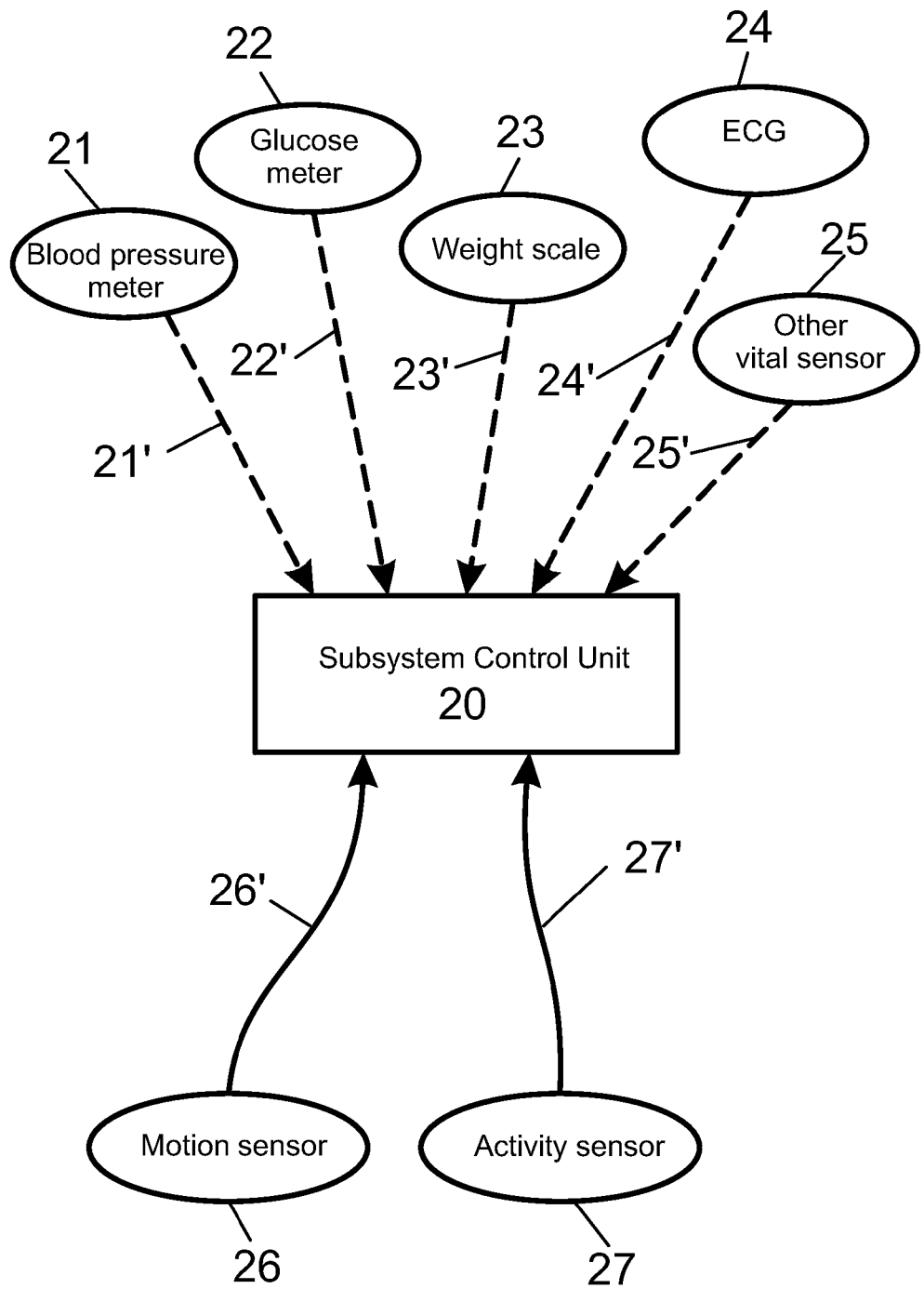
FIG. 2 is a schematic block diagram of the used measuring units according to an embodiment of the present invention.

In a patient side subsystem, as shown in FIG. 2, a subsystem control unit 20 (also called homehub) may be connected to measuring units 21 to 25 for measuring vital signs of the individuals to be monitored and to measuring units 26 and 27 for performing continuous measurement of behavioral data of the individuals to be monitored. The subsystem control unit 20 further is able to receive, store and apply monitoring profiles provided by the central server unit 10.

The measuring units 21 to 25 for measuring vital signs have a communication link to the subsystem control unit 10 as indicated by the dotted lines 21' to 25'. These communication links 21' to 25' may be accomplished by wired communication links or by wireless communication links. The measuring units 21 to 25 for measuring vital signs of the individuals to be monitored may include for example but not exclusively, a blood pressure meter 21 for measuring the blood pressure, a glucometer 22 for measuring the blood glucose, weight scale 23 for determining the weight, an ECG monitor 24 for providing ECG data and other vital sign sensors 25 with the interaction of the monitored person. A part or all of these measuring units 21 to 25 may have a wireless communication link to the subsystem control unit 20 as indicated by the dotted lines 21' to 25'. The wireless communication may be performed by using a radio communication according to the Bluetooth, Zigbee, Wifi or other standardized specifications. Some of the devices that are outside the wireless communication range or do not have a wireless communication capability, may be connected to the subsystem control unit 20 by a communication wire, such as a USB cable or the like. The vital sign measuring devices 21 to 25 need not to be specialized devices, any measuring units available off-the shelf may be suitable for embodiments of the present invention, even those which do not have any connection possibility. In an embodiment, the homehub 20 used in the system must have a manual input capability, to enable the user to input the measuring result obtained from such a measuring unit, e.g. a bathroom weight scale. Using such a device the individual will read the result from the device and input (or type) the value(s) using an input device (keyboard) of the homehub 20. Such a subsystem for assisting elderly people or patients in carrying out vital sign measurement on their own, are known in the prior art such as disclosed in U.S. Pat. No. 7,684,999.

The subsystem control unit 20 is configured to receive and store the results of the distinct measurements of vital signs and of the continuous measurement of behavioral data. The measuring units 26 and 27 for performing continuous measurement of behavioral data of the individuals to be monitored may include, for example, some fix mounted motion sensors 26 for determining the motion and/or location of the individual in a selected area, and/or some body-worn sensors for sensing the activity such as speed and/or acceleration of the motion of a selected body part of the individual for determining the motion activity of the individual. The fix mounted motion sensors 26 may communicate with the subsystem control unit 20 using either a wireless or a wired communication link. In case of the body-worn sensors, in an embodiment, they are communicating with the subsystem control unit 20 using either through a wireless communication link so as not to restrict the wearer in his or her movement in any way. As a wired or wireless communication link, the same or similar communication link may be selected as the ones used for the measuring unit for measuring vital signs.

The fix mounted sensors may be, for example, motion detectors 26 or contact sensors mounted on walls or other pieces of furniture or equipment of the living area of the individuals to be monitored. These sensors are not in direct contact with the monitored person. The contact sensors can have different function in a monitored area. Typical installation points are the front door of the house/apartment, doors which might be useful to know if open or closed (e.g. bathroom door), doors of household equipment (e.g. door of the fridge) and critical places healthcare related monitoring (e.g. if the person keeps all the medication in a closed drawer or box, the door of this holder). Motion sensors, such as passive infrared sensors (PIR sensors) can measure infrared light radiating from objects in its field of view. Actual motion is detected when an infrared source with one temperature changes its position in front of an infrared source with another temperature, so in our case when a human passes the sensor's field of view in the monitored are. If there's a higher amount of motion then a pre-defined threshold, the sensor sends a signal to the subsystem control unit.

The body-worn sensor may be, for example, an activity sensor 27 such as a speed or acceleration sensor fixed to a part of the body. In an embodiment, the activity sensors 27 can be fixed to a hand or arm or to a leg or foot of the wearer. These activity sensors 27 are in direct contact with the monitored person. The body-worn sensor, or Actigraph as it is generally called, is a body-worn equipment, most often worn on the wrist, like a wristwatch. The unit continually records the movement of the equipment itself, therefore the movement of the patient's wrist. This data can be used to calculate the motion of the monitored person (overall activity, step count, etc.).

Figure 3:
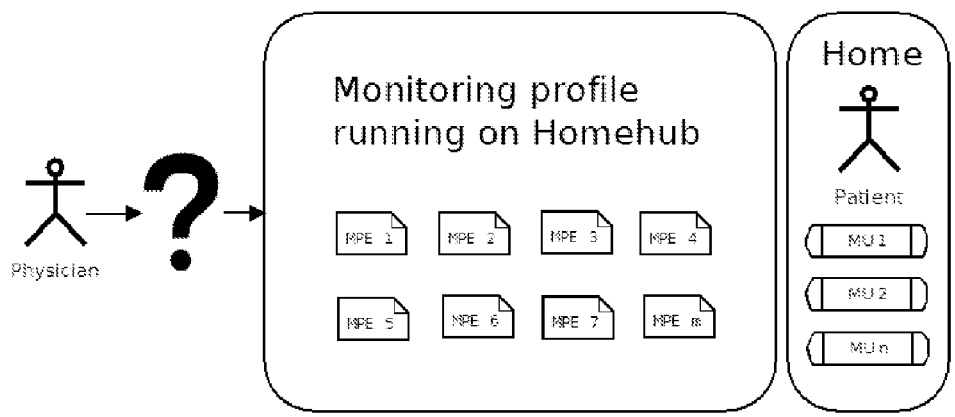
FIG. 3 is a schematic diagram of the composition of the monitoring profile according to an embodiment of the present invention.

The schematic diagram in FIG. 3 illustrates the basic problem of the monitoring profile composition.

On the right side of FIG. 3, there is shown a patient side subsystem located, for example, in the home of the patient, where a subsystem control unit (or homehub) and various measuring units MU1, MU2 to MUn are installed. The number of installed measuring units is not limited. Measuring units may measure vital signs like blood pressure or ECG, or behavioral data like entering a room or doing physical exercises, or abilities like a cognitive test or a reflex examination. For measurement types, in case of which a graphical user interface and an input device is only needed (e.g. a cognitive test), there is no need for a separate measuring unit, the patient side subsystem control unit can carry out the measurement itself.

The whole monitoring and therapy process is described, customized and parameterized in the monitoring profile. The patient side subsystem control unit, e.g. the Homehub is able to receive and store the monitoring profile received from the central server unit and is able to manage the monitoring and therapy process described by the profile.

The monitoring profile consists of numerous monitoring profile elements MPE 1-MPE n. Each monitoring profile element is responsible for representing an elementary measurement specification, or monitoring procedure, or signal processor, or medical rule, or survey, or patient task, as described in the Technical Background section. The whole monitoring and therapy process is described and managed by the totality of the monitoring profile elements.

In order to launch the remote health monitoring and therapy process the physician has to put his intended actions of monitoring, measurements, patient tasks, surveys, and medical rules into monitoring profile elements. This is the problem of composition of the monitoring profile, denoted by the question mark. The question is: how can the physician compose the monitoring profile in a fast, effective, and reliable way, which allows customization and usage of pre-defined templates.

Figure 4:
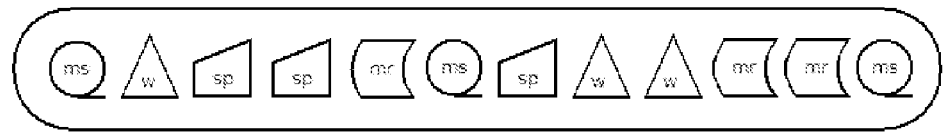
FIG. 4 is a schematic diagram of a flat monitoring profile structure according to an embodiment of the present invention.

The schematic diagram of FIG. 4 displays a possible monitoring profile composition, a so called flat structure, also used by prior art systems.

In this flat structure each monitoring profile element is on the same level of hierarchy. Although this monitoring profile composition is very simple, it has several disadvantages, like:

There is no possibility to define higher-level abstractions.

When composing the monitoring profile, physicians have to select high number of monitoring profile elements and have to modify high number of monitoring profile element parameters.

It is complicated to review an already composed monitoring profile, because high number of monitoring profile elements must be taken into consideration simultaneously.

It is complicated to review and outline the high number of collected low-level data.

The different icons appearing in this figure denote different types of primitive monitoring profile elements. Many possible types of primitive monitoring elements are possible, still, this figure only contains 4 types of them for demonstration purposes. These are measurement specification (denoted by 'ms'), workflow procedure (denoted by 'w'), signal processor (denoted by 'sp'), and medical rule (denoted by 'mr').

Monitoring profile definitions may also contain the following:

The list and configuration details of all the monitoring measuring units, such as what physiological sensors to use, what behavioural sensors to use, and the specific configuration for the sensors.

The list and configuration details of measurement specifications, such as scheduling of the measurements, the used measuring units, the measurement instructions to display on the homehub, and surveys, which must be taken during, before, or after measurement.

The list and configuration details of monitoring procedures, such as the used measuring units, scheduling of data collection, algorithms, which calculate the behavioral attribute based on sensor data, and system reaction to specific scenarios.

The list and configuration details of signal processors doing data analysis, such as disease specific data analysis, detailed configuration, and thresholds for data analysis.

The medical rules and their details, such as detailed configuration, thresholds of predicates, and the severity of warnings, alerts created by decision support rules.

The surveys and survey details, such as scheduling of run, flow and questions of survey, and algorithms, which calculate the result based on the given answers.

The patient tasks, such as scheduling, detailed configuration, and algorithms evaluating the success rate.

The list and configuration details of all the data visualization possibilities, such as graphs showing the interaction of several sensor's data, graphs best visualizing significant change in patient's condition.

The monitoring profile definitions may also contain specific threshold values showing deviation from disease management goals and alert thresholds.

Figure 5:
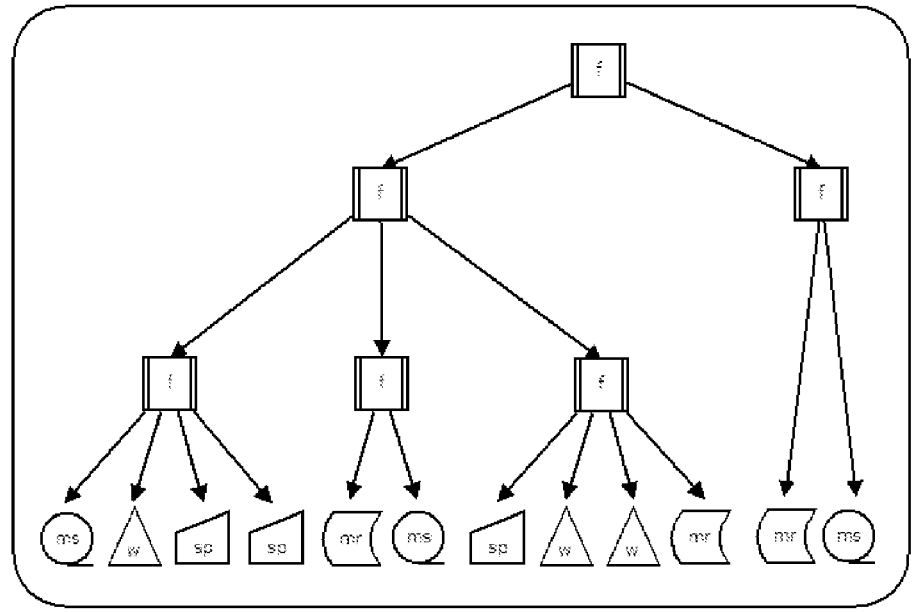
FIG. 5 is a schematic diagram of a hierarchical multi-level monitoring profile structure according to an embodiment of the present invention.

The schematic diagram in FIG. 5 shows a hierarchical multi-level monitoring profile composition. The shown monitoring profile contains many primitive monitoring profile elements (at the bottom of the figure), as seen in FIG. 4, however a new type of elements (denoted by 'f') appears. These monitoring profile elements are higher-level abstract functions. Each abstract function 'f' represents a higher-level operation, higher-level functionality, which is ensured by the child elements of the function. Adding an abstract function template to the monitoring profile entails the addition of all the child elements of the function template.

According to an aspect of the invention, the monitoring profile elements are connected to each other to provide a multi level tree structure consisting of at least two monitoring profile levels, with a higher or top level defining a top-level monitoring profile adapted to a specific health status, and lower or bottom level containing the low-level monitoring profile elements, such as patient related data, monitoring related data, and evaluating process elements.

The patient related data and the monitoring related data may comprise configuration parameters such as listed above in connection with FIG. 4, and the evaluating process elements may comprise software components responsible for the functionality of the monitoring profile elements. The monitoring profile elements are divided according to the tree structure of the multi level monitoring profile and a part of the monitoring profile elements is assigned to the top monitoring profile level and a part of the monitoring profile elements is assigned to the bottom monitoring profile level.

In another embodiment, the multi level monitoring profile comprises at least one intermediate monitoring profile level between the top monitoring profile level and the bottom monitoring profile level and a part of the monitoring profile elements is assigned to the at least one intermediate monitoring profile level.

In the embodiment shown in FIG. 5, there are four monitoring profile levels, a top level, a bottom level and two intermediate levels. The number of the monitoring profile levels for the different top level monitoring profiles (individual patients with different diseases) may be different.

The top level comprises top level parameter elements of the monitoring profile elements and the subordinated (child) levels comprise parameter elements derived from the top level parameter elements of the monitoring profile elements. The bottom level comprises bottom level (raw) data elements of monitoring profile elements and the superimposed (parent) levels comprise data elements derived from the bottom level data elements of the monitoring profile elements The predetermined structures of the different monitoring profile elements assigned to the different monitoring levels and the predetermined connection of the monitoring profile elements may be stored in predetermined default templates. Similarly, the modified structures of the different monitoring profile elements assigned to the different monitoring levels and the modified connection of the monitoring profile elements may be stored in modified templates.

The Multi-level Monitoring Profiles or MMPs contain profile elements in a hierarchical structure. In this structure arbitrary levels of functionality can be declared. At the bottom level parameterised primitive monitoring elements take place, like a signal processor or a medical rule. Higher levels represent higher-level functionalities. The highest-level nodes of the structure are complete therapy and/or monitoring processes (i.e. monitoring profile) adequate to a specific health status. Examples will make this more understandable.

In case of a diabetes diseased patient for instance, the monitoring profile might look like the following. The bottom level primitive monitoring elements are listed in italic style.

Home rehabilitation of diabetes diseased in inchoative stage (monitoring profile)
  Monitoring of physical activity
    Collecting row motion data
      *Motion data measurement specification (workflow)*
  Monitoring trend of physical activity
    Scheduled signal processor calculating the summarized amount of physical activity in a period of time
    Scheduled signal processor calculating the trend of physical activity in a period of time
    Scheduled medical rule, which generates monitoring alert in case of abnormal trend
  Monitoring number of bathroom visits
    Scheduled signal processor calculating the number of bathroom visits in a period of time
    Scheduled signal processor calculating the trend of bathroom visits in a period of time
    Scheduled medical rule, which generates monitoring alert in case of abnormal trend
  Monitoring activity at night
    Signal processor calculating nightly activity
    Medical rule generating alert on high nightly activity
  Monitoring of blood glucose level
    Scheduled blood glucose measurement
      *Scheduled blood glucose measurement specification (workflow)*
    Manually started blood glucose measurement
      *Manual blood glucose measurement specification (workflow)*
    Blood glucose level monitoring
      *Signal processor checking the level of blood glucose, generating alert if limits are exceeded*
    Survey to carry out in case of abnormal glucose level
      *Workflow running the survey*
    Tracking missed measurements
      *Scheduled medical rule computing the required frequency of blood glucose measurements within a day*
      *Signal processor creating monitoring alerts in case of missing measurements*
      *Workflow, which informs the patient about the required frequency of measurements*
  Medication tracking
    Collecting door opening events of medicine cabinet
      *Door opening event measurement specification*
    Check door opening events regularly
      *Signal processor creating monitoring alert in case of forgotten take of medication based on prescriptions of the doctor*
  Diet suggestions
    Scheduled general nutrition suggestions for diabetes
      *Medical rule choosing suggestions adequate to the current state of the patient from a set of suggestions*
      *Scheduled workflow displaying suggestions*
    Suggestion in case of abnormal glucose level
      *Workflow displaying suggestions in this case*

The structure of the MMP is a tree graph of arbitrary levels, where parameter delegation (in direction of leaves) and data delegation (in direction of root node) is taking place. The responsibilities of the nodes are the following.

Leaf nodes at the bottom level are responsible for representing a primitive monitoring element, containing all the parameters of the represented element, generating low-level data, and delegating generated data to the parent node.

Intermediate nodes are responsible for containing underlying lower-level nodes (i.e. a group), determining parameters of child nodes based on parameters of the node using a parameter determining method, delegating determined parameters to child nodes, generating higher-level (parent) data and monitoring events based on lower-level (child) data outputs of child nodes, wherein the parent data is determined by the used data generation method and the data propagated by child nodes, and delegating generated parent data to the parent node.

Top-level nodes are responsible for all the items intermediate nodes are responsible for, except for the delegation of generated data to the parent node, and generating top-level monitoring events, like notifications, warnings and alerts.

An automatic or semi-automatic (where certain user interaction is needed) algorithm parameterises the intermediate and the bottom level elements of the monitoring profile. Parameters of child nodes are determined based on parameters of their parent nodes. During the parameter delegation derived parameter elements may be delegated to each of the subordinated (child) levels. Possible parameter delegation methods include simple delegation, wherein the parameter is delegated downwards as it is without any change, enumerated assign, wherein for every enumerated value of the parent parameter a specific child parameter is assigned, range assign, wherein a child parameter is chosen as a value assigned to the specific range the numeric parent parameter belongs to, calculation, wherein a child parameter is calculated by evaluation of a mathematical formula containing parent parameter(s) as variable(s), and constant delegation, wherein the applied child parameter is defined as a constant in the parent node.

While parameters of the monitoring profile elements are delegated in the direction of leaves in the graph (from the top monitoring profile level in direction to the bottom monitoring profile level), collected or generated data are delegated upwards in the direction of the root node (from the bottom monitoring profile level in direction to the top monitoring profile level). Low-level data are aggregated, so that they build up higher-level data. This aggregation can occur in monitoring profile elements of any intermediate levels of the tree. During the data delegation derived data elements are delegated to each of the superimposed (parent) levels. Possible data generation or aggregation methods are simple delegation, wherein data are delegated upwards as they are, without any change, range assign, wherein parent data are chosen as a value assigned to the specific range the numeric child data belong to, calculation, wherein parent data are calculated by evaluation of a mathematical formula containing data propagated by child nodes as variables, and statistical abstraction, wherein parent data is calculated as a statistical indicator over the population of data propagated by child nodes in a period of time Advantages of the hierarchical multi-level monitoring profile structure with parameter and data delegation are the following:

High number of elements can be added to the monitoring profile easily using predefined high-level abstract functions (i.e. templates).

The automatic parameterization of monitoring profile elements makes the configuration easy, fast and reliable.

The review of an already composed monitoring profile is much more simple and intuitive thanks to the few applied high-level elements (i.e. abstract functions).

Review and interpretation of collected monitoring data is easier due to the high abstraction level of generated higher-order data.

Figures 6, 7:
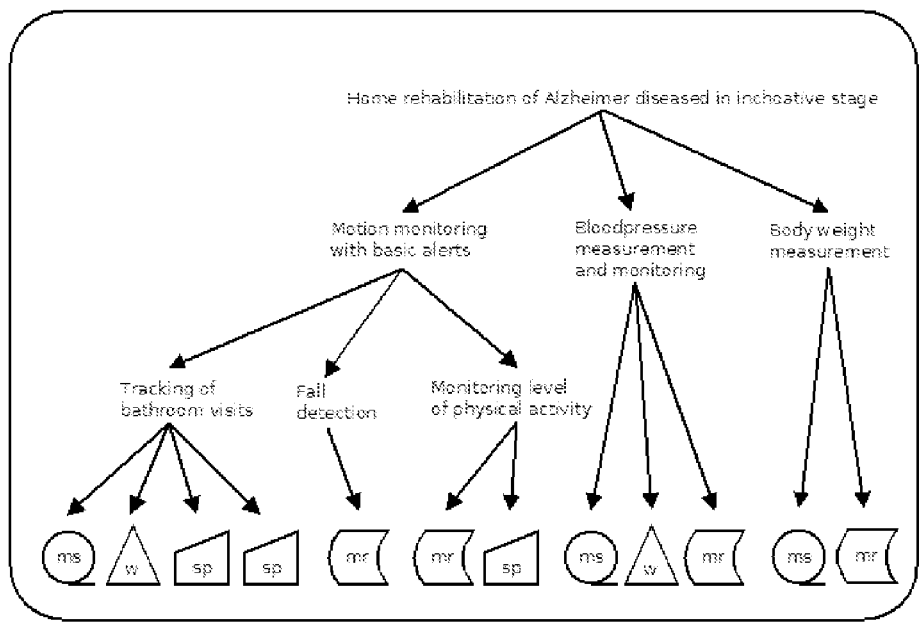
FIG. 6 is a schematic diagram for a simple example of a multi-level monitoring profile according to an embodiment of the present invention.
FIG. 7 is a high-level definition of a monitoring scenario according to an embodiment of the present invention.

A simple example of a multi-level monitoring profile is demonstrated in FIG. 6.

In this figure a simple example of multi-level monitoring profile (MMP) is demonstrated. The top-level monitoring element is labeled as 'Home rehabilitation of Alzheimer diseased in inchoative stage'. In this example the physician may have chosen this single predefined element (template) as the base of the monitoring profile, which entailed the insertion of the whole predefined monitoring element hierarchy (i.e. MMP structure). According to an aspect of the invention, a modified template for the structure of the different monitoring profile elements may be generated and stored in a storage unit for each patient.

Assume the rehabilitation and monitoring process consists of three major functionalities; motion monitoring with basic alerts, blood pressure measurement and monitoring, and body weight measurement. The motion monitoring consists of three intermediate level monitoring processes, like tracking of bathroom visits, fall detection, and monitoring the level of physical activity. The elements of the corresponding monitoring profile and their hierarchy, as can be seen in the figure, reflect this structure. Low-level monitoring elements (i.e. leaves of the tree) are primitive monitoring elements, like a measurement specification 'ms', workflow procedure 'w', signal processor 'sp', or a medical rule 'mr'.

The example MMP contains seven abstract functions (Home rehabilitation of Alzheimer diseased in inchoative stage, motion monitoring with basic alerts, blood pressure measurement and monitoring, and body weight measurement, tracking of bathroom visits, fall detection, and monitoring the level of physical activity), which are ensured by twelve low-level primitive elements listed in the bottom row.

FIG. 7 represents/illustrates a high-level definition of a monitoring scenario, which shows an example of how the configuration and the high level definition of a monitoring scenario, given usually by a general healthcare professional flows down to monitoring profile elements of high, intermediate, and low levels, according to the monitoring template predefined by the expert healthcare professional. This flow down can be seen in the column called 'Configuration'. The figure also shows, how the monitoring data flows up from the lower, detailed, specific, row level to higher levels of abstraction. This flow up is shown in the column called 'Monitoring data, monitoring event'. In this example only a part of a monitoring profile is presented, a single branch of a whole monitoring profile tree structure. The different actors in the system have the freedom to configure the monitoring elements on any level they want, still, the predefined default templates provide a solid base. A modified template for the structure of the different monitoring profile elements may be stored in a storage unit for each patient, so the healthcare professional is able to re-use an already configured monitoring profile instead of configuring a new one based on one of the predefined default templates.

Due to the disadvantages of the prior art systems and methods, there is a continuous need for providing a system and a method, which effectively supports healthcare professionals in composition and customization of the whole monitoring profile, high-level overview, and change of a monitoring profile, high-level data presentation, and, through usage of predefined hierarchical, multi-level structures, so called multi-level monitoring profile (MMP) definitions.

In an exemplary embodiment of the invention, a health monitoring system is proposed, the system comprising a patient side subsystem, a health care providing side subsystem, a server station with a database and a communication system for providing communication links between the system elements, comprising a monitoring profile consisting of profile elements being connected to each other in a predetermined manner, the monitoring profile elements comprising patient related data, monitoring related data, and evaluating process elements.

According to the improvement of the invention the system is also wherein the monitoring profile elements are connected to each other to provide a multi level tree structure consisting of at least two monitoring profile levels, with a highest level defining a top monitoring profile level and lowest level defining a bottom monitoring profile level, wherein the monitoring profile elements, such as patient related data, monitoring related data, and evaluating process elements, are divided according to the tree structure of the multi level monitoring profile and a part of the monitoring profile elements are assigned to the top monitoring profile level and a part of the monitoring profile elements are assigned to the bottom monitoring profile level.

In another exemplary embodiment of the invention a method is proposed for operating such a health monitoring system. The method comprises the steps of providing a monitoring profile consisting of profile elements being connected to each other in a predetermined manner, the monitoring profile elements comprising patient related data, monitoring related data, evaluation process elements.

The method is further wherein the monitoring profile elements are connected to each other to provide a multi level tree structure consisting of at least two monitoring profile levels, with a highest level defining a top-level monitoring profile adapted to a specific health status and lowest level containing the low-level monitoring profile elements, such as patient related data, monitoring related data, evaluation process elements are divided according to the tree structure of the multi level monitoring profile and a part of the monitoring profile elements is assigned to the top monitoring profile level and a part of the monitoring profile elements is assigned to the bottom monitoring profile level.

The proposed layered multilevel monitoring profile structure, provides the ability of high level composition, configuration and review of monitoring and therapy profiles, while maintaining the ability of simultaneous evaluation and influence of each of the lower level monitoring profile elements.

Further advantageous embodiments of the invention are provided in the depending claims.

The proposed multi level structure has many important advantages:

1. The setting up of a monitoring profile means composing a monitoring profile from numerous monitoring elements and parameterization of these elements. In case of multiple monitoring elements the setup may be very complicated. In contrast to this, when using MMPs only few high-level elements must be chosen, as initial template. The underlying structure of elements is deployed recursively.

For instance, choosing the 'Home rehabilitation of diabetes diseased in inchoative stage' monitoring profile template, all the measurement specifications, monitoring procedures, signal processors, medical rules, surveys and tasks are added to the monitoring and therapy process. The newly created monitoring profile can be configured, customized and finally it will be transmitted to the patient side monitoring terminal (i.e. homehub) in order to be executed.

2. In case of a more sophisticated monitoring profile, the parameterisation of the numerous applied monitoring elements is a huge, expert-demanding work. This work, where all parameters of all monitoring elements must be set up one by one manually, is not only time-consuming, but also increases the possibility of configuration errors. In contrast to this, when using MMPs, parameter delegation can be applied, which reduces the work of parameterization.

Parameter delegation is, when a parameter of a higher-level node determines parameters of underlying lower-level nodes in the MMP. For instance the 'severity' parameter of a behaviour-monitoring package set up by the doctor can automatically determine and set up the parameters (e.g. scheduling, timeout values, alert thresholds) of monitoring procedures, signal processors, medical rules belonging to the behaviour-monitoring package.

3. Without using MMPs, overview/review of a monitoring profile constructed earlier is complicated since the expert only sees the low-level monitoring elements, which he/she should put together in mind in order to have a high-level overlook. In contrast to this, when using MMPs, medical expert can have a fast and accurate overlook of the running monitoring profile by having a look at the few top-level monitoring elements in the MMP. For instance he/she will see top-level elements, like 'Home rehabilitation of diabetes diseased in inchoative stage' or 'Monitoring of physical activity'.

4. Viewing, analyzing, and inspecting of low-level measurement data is very complicated for human actors of the system. For instance, the human overview of the low-level outputs of motion sensors, containing timestamps (e.g. time of motion event) and zone identifiers (e.g. place of motion) is hardly possible, regarding the high amount of motion data generated every day. In contrast to this, when using MMPs, low-level data is integrated and build up higher-level data. This aggregation can occur on any intermediate level of the MMP. For instance many low-level motion events in bathroom in a continuous period of time are aggregated to a monitoring event data called 'bathroom visit'. When 'bathroom visit' data is generated too frequently, a new monitoring event data called 'unusually high number of bathroom visits' is generated on a higher level in the MMP. The top-level monitoring event (alert) presented to the doctor is 'unusual behavior'. He/she sees this alert as a high-level first approach, in addition he/she is able to drill down and find out the causes and details of this high-level alert.

Further advantages of the concept:

MMPs enable healthcare professionals with different expertise on medical and technical details to effectively manage patients with different chronic diseases and different conditions.

The users can interact with the system in the level of detail they can manage, both for configuration, and reading data.

Contrary to the system described, current systems need significant doctoral, expert or personal attendance increasing error factors while the result of the present development is a system integrating medical expertise, therefore, efficiency and reliability grows and the opportunity of errors decreases.

Most of the current systems concentrate on one singular approach, handling all the cases in a general fashion, while the MMPS based system can effectively monitor and telesupervise several fields and disease groups (stroke, dementia, depression) simultaneously.

Semi-automatic definition of a customized disease specific monitoring plan can be executed by a general healthcare professional, still benefiting from the disease specific medical knowledge embedded in the system.

Case specific data analysis is allowed, based on the methods previously defined by disease and monitoring experts.

Pre-defined data visualization is possible, most suitable for the patient's case, so that the healthcare professional responsible for the case does not have to re-invent the best ways to visualize data.

A case specific, pattern based decision support is available for the general healthcare professional.

The referring physician can define a much more sophisticated monitoring profile setup for a patient, using the expert, disease specific information gathered in the system, thus the quality of the patient management is higher.

The template-based definition/management can speed up the processes, enabling the healthcare professional to handle more cases, which increases productivity and cost-efficiency.

Healthcare professionals with general, no disease specific knowledge can handle a much wider range of patients, which also increases productivity and accessibility.

This written description uses examples to disclose embodiments of the present invention, including the best mode, and also to enable any person skilled in the art to make and use the invention. The patentable scope of the present invention is defined by the claims, and may include other examples that occur to those skilled in the art. Such other examples are intended to be within the scope of the claims if they have structural elements that do not differ from the literal language of the claims, or if they include equivalent structural elements with insubstantial differences from the literal languages of the claims.

What is claimed is:

1. A health monitoring system comprising a patient side subsystem, a health care provider side subsystem, and a server station with a database and a communication system for providing communication links between the system elements, the patient side subsystem configured to periodically receive and apply a monitoring profile from the server station, the monitoring profile consisting of profile elements being connected to each other in a predetermined manner, the monitoring profile elements comprising:
- patient related data;
- monitoring related data; and
- evaluating process elements,
- wherein the monitoring profile elements are connected to each other to provide a multi level tree structure comprising at least two monitoring profile levels comprising:
  - a higher or top level defining a top-level monitoring profile; and
  - a lower or bottom level containing the low-level monitoring profile elements,
- wherein the monitoring profile elements are divided according to the tree structure of the multi level monitoring profile and a part of the monitoring profile elements is assigned to the top monitoring profile level and a part of the monitoring profile elements is assigned to the bottom monitoring profile level and wherein the tree structure of the multi level monitoring profile is stored in the health monitoring system in a template.

2. The system of claim 1, wherein the tree structure of the multi level monitoring profile comprises at least one intermediate monitoring profile level between the top monitoring profile level and the bottom monitoring profile level and a part of the monitoring profile elements is assigned to the at least one intermediate monitoring profile level.

3. The system of claim 1, wherein the number of the monitoring profile levels may be different for the different top level monitoring profiles.

4. The system of claim 1, wherein the top level elements comprise top level parameters and the parameters of the sub-ordinated (child) level elements are derived from the parameters of the parent-level elements.

5. The system of claim 1, wherein the bottom level elements are configured to collect bottom level (row) data and the superimposed (parent) level elements are configured to generate derived (higher order) data from the data collected by the associated child elements.

6. The system of claim 1, wherein predetermined structures of the different monitoring profile elements assigned to the different monitoring levels and the predetermined connection of the monitoring profile elements are stored in predetermined default templates.

7. The system of claim 1, wherein modified structures of the different monitoring profile elements assigned to the different monitoring levels and the modified connection of the monitoring profile elements are stored in modified templates.

8. A method for operating a health monitoring system, the monitoring system comprises system elements including a patient side subsystem, a health care provider side subsystem, and a server station with a database and a communication system for providing communication links between the system elements, the method comprising:
- providing a template to be stored in the server station, the template comprising a monitoring profile, the monitoring profile consisting of profile elements being connected to each other in a predetermined manner, the monitoring profile elements comprising patient related data, monitoring related data, and evaluation process elements, wherein the monitoring profile elements are connected to each other to provide a multi level tree structure consisting of at least two monitoring profile levels comprising a higher or top level defining a top-level monitoring profile adapted to a specific health status, and a lower or bottom level containing the low-level monitoring profile elements, wherein the monitoring profile elements are divided according to the tree structure of the multi level monitoring profile and a part of the monitoring profile elements is assigned to the top monitoring profile level and a part of the monitoring profile elements is assigned to the bottom monitoring profile level;
- using a health care provider side subsystem, selecting the template or creating, storing and selecting a modified template in the server station;
- communicating the selected template or modified template from the server station to the patient side subsystem; and
- storing and applying the selected template or modified template in the patient side subsystem.

9. The method of claim 8, wherein the tree structure of the multi level monitoring profile comprises at least one intermediate monitoring profile level between the top monitoring profile level and the bottom monitoring profile level and a part of the monitoring profile elements are assigned to the at least one inter-mediate monitoring profile level.

10. The method of claim 8, wherein the number of the monitoring profile levels may be different for the different top level monitoring profiles.

11. The method of claim 8, wherein parameters of the top level monitoring profile elements are delegated from the top monitoring profile level in direction to the bottom monitoring profile level.

12. The method of claim 11, wherein during the parameter delegation derived parameter delegated derived parameters are delegated to the subordinated (child) levels.

13. The method of claim 8, wherein data collected by the bottom level monitoring profile elements are delegated from the bottom monitoring profile level in direction to the top monitoring profile level.

14. The method of claim 13, wherein during the data delegation de-rived (higher-order) data elements are delegated to the superimposed (parent) levels.

15. The method of claim 8, wherein predetermined structures of the different monitoring profile elements assigned to the different monitoring levels and the predetermined connection of the monitoring profile elements are stored in predetermined default templates.

16. The method of claim 8, wherein modified structures of the different monitoring profile elements assigned to the different monitoring levels are stored in modified templates.

17. The method of claim 8, wherein a patient specific monitoring profile is derived from a predetermined template and stored for a specific patient.

* * * * *

UNITED STATES PATENT AND TRADEMARK OFFICE
CERTIFICATE OF CORRECTION

PATENT NO. : 8,990,260 B2  
APPLICATION NO. : 13/631312  
DATED : March 24, 2015  
INVENTOR(S) : Devenyi et al.

Page 1 of 1

It is certified that error appears in the above-identified patent and that said Letters Patent is hereby corrected as shown below:

In the Claims

In Column 16, Line 18, in Claim 8, delete "using a" and insert -- using the --, therefor.

In Column 16, Line 39, in Claim 12, delete "derived parameter delegated derived parameters" and insert -- derived parameters --, therefor.

Signed and Sealed this  
Tenth Day of November, 2015

Michelle K. Lee  
*Director of the United States Patent and Trademark Office*